(12) United States Patent
Nemoto et al.

(10) Patent No.: US 7,998,942 B2
(45) Date of Patent: Aug. 16, 2011

(54) EYE DROP PREPARATION COMPRISING XANTHAN GUM AND TERPENOID

(75) Inventors: Fukiko Nemoto, Kobe (JP); Koji Doi, Kobe (JP); Hiroshii Aki, Kobe (JP)

(73) Assignee: Senju Pharamaceutical Co., Ltd., Osaka (JP)

( * ) Notice: Subject to any disclaimer, the term of this patent is extended or adjusted under 35 U.S.C. 154(b) by 190 days.

(21) Appl. No.: 11/988,489

(22) PCT Filed: Jul. 11, 2006

(86) PCT No.: PCT/JP2006/314129
§ 371 (c)(1),
(2), (4) Date: Jan. 9, 2008

(87) PCT Pub. No.: WO2007/007894
PCT Pub. Date: Jan. 18, 2007

(65) Prior Publication Data
US 2009/0054531 A1  Feb. 26, 2009

(30) Foreign Application Priority Data
Jul. 11, 2005  (JP) .................................. 2005-201871

(51) Int. Cl.
*A61K 31/715* (2006.01)
*A61K 31/05* (2006.01)

(52) U.S. Cl. ............................ 514/54; 514/731; 514/912

(58) Field of Classification Search .................... 514/54, 514/731, 912
See application file for complete search history.

(56) References Cited

U.S. PATENT DOCUMENTS

| | | | |
|---|---|---|---|
| 4,136,177 A | 1/1979 | Lin et al. | |
| 5,888,515 A | 3/1999 | Albert et al. | |
| 6,147,081 A * | 11/2000 | Noyori et al. | ................ 514/277 |
| 6,156,785 A | 12/2000 | Stefansson et al. | |
| 6,174,524 B1 | 1/2001 | Bawa et al. | |
| 6,264,935 B1 | 7/2001 | Chastaing et al. | |
| 6,277,365 B1 | 8/2001 | Ellis et al. | |
| 2002/0094981 A1 | 7/2002 | Ponticello et al. | |
| 2003/0059446 A1 | 3/2003 | Kulkarni et al. | |
| 2003/0195179 A1 | 10/2003 | Sawa | |

FOREIGN PATENT DOCUMENTS

| | | |
|---|---|---|
| EP | 0 392 845 | 10/1990 |
| EP | 1 022 017 | 7/2000 |
| EP | 1 797 888 | 6/2007 |
| JP | 8-333227 | 12/1996 |
| JP | 2000-273061 | 10/2000 |
| JP | 2002-3364 | 1/2002 |
| JP | 2002-003364 | 1/2002 |
| JP | 2003-128583 | 5/2003 |
| WO | 99/00133 | 1/1999 |
| WO | 00/04898 | 2/2000 |
| WO | 00/04899 | 2/2000 |
| WO | 02/15878 | 2/2002 |
| WO | 03/080011 | 10/2003 |

OTHER PUBLICATIONS

International Search Report issued Sep. 12, 2006 in the International (PCT) Application of which the present application is the U.S. National Stage.

Chinese Office Action issued Jan. 8, 2010 in corresponding Chinese Application No. 2006-80023984 (with English translation).

* cited by examiner

*Primary Examiner* — Zohreh Fay
(74) *Attorney, Agent, or Firm* — Wenderoth, Lind & Ponack, L.L.P.

(57) ABSTRACT

The present invention provides an ophthalmic solution containing xanthan gum and terpenoid, which shows a suppressed decrease in the terpenoid content, by the addition of xanthan gum to an ophthalmic solution containing terpenoid.

4 Claims, No Drawings

US 7,998,942 B2

EYE DROP PREPARATION COMPRISING XANTHAN GUM AND TERPENOID

This application is a U.S. national stage of International Application No. PCT/JP2006/314129 filed Jul. 11, 2006.

TECHNICAL FIELD

The present invention relates to an ophthalmic solution comprising xanthan gum and terpenoid, which shows a suppressed decrease in the terpenoid content.

BACKGROUND ART

Many of general ophthalmic solutions contain terpenoids such as menthol, camphor, borneol and the like as algefacients in order to provide a cool sensation and a refreshing feel upon instillation. While plastic containers are generally used for such ophthalmic solutions, the terpenoid content is known to decrease when a drug containing terpenoid is filled and preserved in a plastic container. To solve this problem, JP-A-2000-273061 discloses an oil-in-water emulsion ophthalmic solution in a plastic container wherein decrease in the terpenoid content is suppressed. Moreover, JP-A-2002-003364 discloses a method of suppressing adsorption of algefacients such as menthol and the like to a container, which comprises adding polyvalent alcohol into a unit-dose (disposable) eyedrop container.

Lacrimal fluid is known to have pseudoplasticity. That is, the viscosity of lacrimal fluid decreases when a force is applied by blinking, and increases when the force is not applied. Therefore, lacrimal fluid has unique property in that it has low viscosity and becomes thin during blinking to facilitate blinking, but it becomes highly viscose before and after blinking to cover the eye surface for protection. As a polymer compound showing such pseudoplasticity, xanthan gum is known.

As an ophthalmic composition containing xanthan gum, the following have been reported. For example, an ophthalmic composition containing echothiopate iodide and xanthan gum is disclosed, and xanthan gum has been reported to enhance the treatment effect of echothiopate iodide (U.S. Pat. No. 4,136,177). In addition, an ophthalmic composition containing xanthan gum and a carbonic anhydrase inhibitor has been disclosed, where xanthan gum is used to improve ophthalmic bioavailability of the carbonic anhydrase inhibitor (JP-T-2001-508035, JP-T-2002-501017, JP-T-2002-506461). For the purpose of improving ophthalmic bioavailability of a drug, xanthan gum is used, and an ophthalmic composition containing a carbonic anhydrase inhibitor, a prostaglandin derivative and xanthan gum has been disclosed (JP-T-2002-501533, JP-T-2002-521332, JP-T-2002-521333). An ophthalmic composition containing quaternary nitrogen-containing ethoxylated glycoside and xanthan gum has been disclosed for the treatment of dry eye (JP-T-2001-516713). In addition, an ophthalmic composition containing xanthan gum, which is gelated upon contact with the eye, has been disclosed (JP-T-2002-510654). Moreover, U.S. Pat. No. 6,623,751 reports in connection with skin patches that can be adapted to the shape of around the eye, forehead, nose, the mouth and the like, a patch containing a hydrophilic gelling system in an aqueous phase. Example 3 of U.S. Pat. No. 6,623,751 reports a patch containing xanthan gum and menthol.

However, there has been no report on an ophthalmic solution comprising xanthan gum and terpenoid. Moreover, suppression of decrease in the terpenoid content by xanthan gum in an ophthalmic solution has not been reported.

DISCLOSURE OF THE INVENTION

An object of the present invention is to provide an ophthalmic solution comprising terpenoid, which shows a suppressed decrease in the terpenoid content. Another object of the present invention is to provide a method for suppressing a decrease in the content of terpenoid in an ophthalmic solution comprising terpenoid.

The present inventors have conducted intensive studies in an attempt to achieve the aforementioned objects and found that addition of xanthan gum to an ophthalmic solution comprising terpenoid can suppress a decrease in the terpenoid content. The present inventors conducted further studies based on this finding and accomplished the present invention.

Accordingly, the present invention relates to
(1) an ophthalmic solution comprising xanthan gum and terpenoid;
(2) the ophthalmic solution of (1) above, wherein the terpenoid is menthol and/or camphor;
(3) the ophthalmic solution of (1) or (2) above, wherein the concentration of the xanthan gum is 0.2-0.7 w/v %;
(4) the ophthalmic solution of any one of (1) to (3) above, wherein the concentration of the terpenoid is 0.002-0.05 w/v %;
(5) the ophthalmic solution of any one of (1) to (4) above, wherein a container used therefor is a plastic container; and
(6) a method for suppressing a decrease in the content of terpenoid, which comprises adding xanthan gum to an ophthalmic solution comprising terpenoid.

According to the present invention, an ophthalmic solution showing a suppressed decrease in the terpenoid content can be provided by adding xanthan gum. Moreover, a method for suppressing decrease in the content of terpenoid in an ophthalmic solution, which comprises adding xanthan gum to an ophthalmic solution containing terpenoid, can be provided. Furthermore, the ophthalmic solution of the present invention provides an excellent feel during use due to a viscous feel free of stickiness and a refreshing feel it provides in combination, since it comprises xanthan gum and terpenoid.

BEST MODE FOR EMBODYING THE INVENTION

The present invention is described in more detail in the following.

The ophthalmic solution of the present invention encompasses aqueous formulations that can be administered to the eye, for example, aqueous ophthalmic solutions and aqueous ophthalmic suspensions.

While a container to be used for the ophthalmic solution of the present invention is not particularly limited insofar as it is usable for the aqueous formulations, plastic containers are preferable. Examples of the materials of the plastic containers include polyethylene terephthalate, polyethylene, polypropylene and the like. Polyethylene terephthalate is particularly preferable.

Xanthan gum to be used for the ophthalmic solution of the present invention generally has an average molecular weight of 100000-50000000, preferably 200000-20000000, and particularly preferably 1000000-10000000. As the xanthan gum, ECHO GUM series such as ECHO GUM T, ECHO GUM F and the like that are commercially available from DAINIPPON SUMITOMO PHARMACEUTICAL CO., LTD.; SAN-ACE series such as SAN-ACE NXG-S and the like commercially available from San-Ei Gen F.F.I. Inc.; KELTROL series such as KELTROL CG, KELTROL CG-T and the like commercially available from Sansho Co., Ltd.; and the like are used, with preference given to ECHO GUM T and KELTROL CG-T.

The xanthan gum in the ophthalmic solution of the present invention has a concentration of generally 0.01-1.5 w/v %, preferably 0.1-1 w/v %, more preferably 0.15-1 w/v %, particularly preferably 0.2-0.7 w/v %, and especially preferably 0.2-0.6 w/v %, in view of suppression of decrease in the terpenoid content. An ophthalmic solution having a xanthan gum concentration of 1.5 w/v % or lower can be produced easily because it has suitable viscosity and allows filtration sterilization under general conditions.

Examples of terpenoids to be used for the ophthalmic solution of the present invention include monoterpenes (menthols (l-menthol, d-menthol, dl-menthol and the like), camphors (l-camphor, d-camphor, dl-camphor and the like), borneol, geraniol, cineol, anethole, limonene, eugenol and the like); sesquiterpenes (farnesol, nerolidol and the like); diterpenes (phytol, cembrene and the like); etc., with preference given to menthol and camphor. These are used in combination of one or more kinds thereof.

The terpenoid concentration of the ophthalmic solution of the present invention upon preparation is generally 0.0002-0.2 w/v %, preferably 0.001-0.1 w/v %, and particularly preferably 0.002-0.05 w/v %.

For suppression of decrease in the terpenoid content, the weight ratio of terpenoid to xanthan gum in the ophthalmic solution of the present invention upon preparation is preferably 1:1000-1:1 and more preferably 1:100-1:10 when the terpenoid concentration is 0.001-0.1 w/v %. When the terpenoid concentration is 0.002-0.05 w/v %, the weight ratio is preferably 1:350-1:4 and more preferably 1:100-1:10.

The ophthalmic solution of the present invention can contain various additives as appropriate, such as buffer, isotonicity agent, preservative, solubilizing agent, stabilizer, chelating agent, thickener, pH adjusting agent and the like.

As the buffer, for example, boric acid or a salt thereof (sodium borate, etc.), citric acid or a salt thereof (sodium citrate, etc.), tartaric acid or a salt thereof (sodium tartrate, etc.), gluconic acid or a salt thereof (sodium gluconate, etc.), acetic acid or a salt thereof (sodium acetate, etc.), phosphoric acid or a salt thereof (sodium hydrogenphosphate, sodium dihydrogenphosphate, etc.), various amino acids such as glutamic acid, ε-aminocaproic acid and the like and tris buffer, etc. can be mentioned. They are used in a combination of one or more kinds thereof.

As the isotonicity agent, for example, sorbitol, glucose, mannitol, glycerol, propylene glycol, sodium chloride, potassium chloride and the like can be mentioned.

As the preservative, for example, paraoxybenzoates, benzalkonium chloride, benzethonium chloride, benzyl alcohol, sorbic acid or a salt thereof, chlorhexidine or a salt thereof, sodium dehydroacetate, cetylpyridinium chloride, alkyldiaminoethylglycine hydrochloride, chlorobutanol and the like can be mentioned. They are used in a combination of one or more kinds thereof.

As the solubilizing agent, for example, nonionic surfactants such as sorbitan polyoxyethylene fatty acid esters (polysorbate 80 and the like), polyoxyethylene hydrogenated castor oil, polyoxyethylene monostearate (polyoxyl stearate 40 and the like), water-soluble polymers such as polyethylene glycol (macrogol 4000 and the like), polyvinylpyrrolidone and the like, propylene glycol, cyclodextrins, and the like can be mentioned.

As the stabilizer, for example, disodium edetate, thiosodiumz sulfate, ascorbic acid, cyclodextrins, condensed phosphoric acid or a salt thereof, sulfite, citric acid or a salt thereof, dibutylhydroxytoluene and the like can be mentioned.

As the chelating agent, for example, sodium edetate, sodium citrate, condensed phosphoric acid or a salt thereof (condensed sodium phosphate etc.) and the like can be mentioned.

As the thickener, for example, methylcellulose, hydroxyethylcellulose, hydroxypropylcellulose, hydroxypropylmethylcellulose, sodium carboxymethylcellulose, polyvinylpyrrolidone, polyvinyl alcohol, polyethylene glycol, hyaluronic acid and the like can be mentioned.

As the pH adjusting agent, for example, sodium hydroxide, potassium hydroxide, sodium carbonate, sodium hydrogencarbonate, boric acid or a salt thereof (sodium borate), hydrochloric acid, citric acid or a salt thereof (sodium citrate, sodium dihydrogen citrate etc.), phosphoric acid or a salt thereof (sodium dihydrogen phosphate, potassium dihydrogen phosphate etc.), acetic acid or a salt thereof (sodium acetate, ammonium acetate etc.), tartaric acid or a salt thereof (sodium tartrate etc.) and the like can be mentioned.

The ophthalmic solution of the present invention is prepared to have pH 3-10 and preferably pH 5-8.

The ophthalmic solution of the present invention may contain, insofar as the objects of the invention are not impaired, one or more kinds of medicinal components selected from anti-inflammatory agents (allantoin, pranoprofen and the like), decongestants (naphazoline hydrochloride and the like), ocular muscle modulators (neostigmine methylsulfate and the like), astringent agents (zinc sulfate and the like), antihistamine agents (chlorpheniramine maleate and the like), antiallergic agents (sodium cromoglycate and the like), vitamins (panthenol and the like), amino acids, and the like.

As the amino acid, for example, glycine, alanine, valine, leucine, isoleucine, phenylalanine, proline, serine, threonine, tyrosine, asparagine, glutamine, lysin, arginine, tryptophan, histidine, cysteine, methionine, aspartic acid, glutamic acid, aminoethylsulfonic acid, and a pharmacologically acceptable salt thereof can be mentioned. As the salt, for example, sodium salt, potassium salt, calcium salt and magnesium salt can be mentioned. These are used in a combination of one or more kinds thereof.

Administration period of the ophthalmic solution of the present invention is not limited. The ophthalmic solution can be suitably administered to an administration subject based on the clinically employed amount as a standard. The blending ratio of the ophthalmic solution of the present invention and the above-mentioned medicinal components can be suitably selected in consideration of the administration subject, target, disease, symptom, combination, and the like. For example, when the administration subject is a human, the above-mentioned medicinal components may be used in a proportion of 0.0006-5 w/v % relative to the ophthalmic solution of the present invention.

The ophthalmic solution of the present invention can be used as both ethical drugs and non-prescription drugs. In addition, it can also be used as an ophthalmic solution for contact lenses or a contact lens solution used when wearing contact lenses. The ophthalmic solution of the present invention can also be used as an ophthalmic solution for the prophylaxis or improvement of eye fatigue, dryness of eye, blurred vision, ocular itching, conjunctival hyperemia, uncomfortableness by wearing contact lenses, and the like. Moreover, the ophthalmic solution of the present invention can be used as an artificial lacrimal fluid to supplement lacrimal fluid (dryness of the eye) and the like.

For example, when the ophthalmic solution of the present invention is used for an adult, it is preferably administered in an amount of 2-3 drops per installation and 5 or 6 times per day, as an ophthalmic solution containing terpenoid in a proportion of preferably 0.001-0.1 w/v % and particularly preferably 0.002-0.05 w/v %.

The ophthalmic solution of the present invention exhibits a viscous feel free of stickiness because it contains xanthan gum, which shows pseudoplasticity. Moreover, the ophthalmic solution of the present invention also provides a cool sensation and refreshing feel because it contains terpenoid as an algefacient.

The present invention provides a method for suppressing decrease in the terpenoid content, which comprises adding xanthan gum to an ophthalmic solution containing terpenoid.

EXAMPLES

While the present invention is described in detail in the following by referring to Examples and Experimental Examples, which are not to be construed as limitative.

Experimental Example 1

Terpenoid Content Decrease-Suppressive Effect of Xanthan Gum in Polyethylene Terephthalate Eyedrop Container 1. Preparation Method Sodium chloride was dissolved in purified water at ambient temperature. While mildly stirring the aqueous solution in a homomixer (T. K. Robomix, Tokushu Kika Kogyo Co., Ltd.), xanthan gum (ECHO GUM T: registered trade mark, DAIN-IPPON SUMITOMO PHARMACEUTICAL CO., LTD.) was gradually added and the mixture was stirred at 15,000 rpm for one hour. l-Menthol (The Japanese Pharmacopoeia Fourteenth Edition) or dl-camphor (The Japanese Pharmacopoeia Fourteenth Edition) was added to this aqueous solution at room temperature and the mixture was stirred at 8,000 rpm for 10 min to allow dissolution. The aqueous solution was filtered through a membrane filter (0.45 μm pore diameter, Pressure Filter, manufactured by Millipore) to give ophthalmic solutions of Examples 1 to 4. In addition, ophthalmic solutions of Comparative Examples 1 and 2 were obtained by an operation in the same manner except addition of xanthan gum.

TABLE 1

| Components added (g/100 mL) | Ex. 1 | Ex. 2 | Ex. 3 | Ex. 4 | Comp. Ex. 1 | Comp. Ex. 2 |
| --- | --- | --- | --- | --- | --- | --- |
| Xanthan gum | 0.2 | 0.5 | 0.7 | 0.5 | — | — |
| Sodium chloride | 0.9 | 0.9 | 0.9 | 0.9 | 0.9 | 0.9 |
| l-Menthol | 0.01 | 0.01 | 0.01 | — | 0.01 | — |
| dl-Camphor | — | — | — | 0.01 | — | 0.01 |
| Purified water | e.q. | e.q. | e.q. | e.q. | e.q. | e.q. |

2. Test Method

The ophthalmic solutions of Examples 1 to 4 and Comparative Examples 1 and 2 were each filled in a 15 mL polyethylene terephthalate eyedrop container and preserved at 60° C. for 2 days. The l-menthol and dl-camphor contents of each sample were measured before and after preservation. The quantification method of l-menthol and dl-camphor is as follows.

A sample (2 mL) was precisely measured, and precisely 2 mL of chloroform was added thereto. The mixture was then vigorously shaken, the chloroform layer was separated and used as a sample solution. Separately, 0.02 g of l-menthol standard product was precisely measured, and chloroform was added thereto to precisely 20 mL. This solution (2 mL) was precisely measured off, chloroform was added thereto to precisely 20 mL, and the solution was used as an l-menthol standard solution. Moreover, 0.02 g of dl-camphor standard product was precisely measured, and chloroform was added thereto to precisely 20 mL. This solution (2 mL) was precisely measured off, chloroform was added thereto to precisely 20 mL, and the solution was used as a dl-camphor standard solution. The sample solution and the standard solution (5 μL) were tested by gas chromatography. The contents of l-menthol and dl-camphor were determined from the peak areas thereof.

l-Menthol or dl-camphor content (W/V %) in sample solution=measured amount (g) of standard product×$A_T/A_S$/2

$A_T$: Peak area of l-menthol or dl-camphor in sample solution $A_S$: Peak area of l-menthol or dl-camphor in standard solution Gas chromatography conditions System: GC-2010 (Shimadzu Corporation)

Detector: Hydrogen flame ionization detector

Column: PEG 20 M 20% Gaschrom Q 60/80 mesh 3 mm×2 m glass column (GL Science)

Column temperature: 150° C.

Detector temperature: 200° C.

Injection temperature: 200° C.

Flow rate: arranged to attain l-menthol retention time of about 8 minutes

3. Test Results

As shown in Table 2, the l-menthol residual ratios increased in Examples 1 to 3 as compared to Comparative Example 1. An l-menthol content decrease-suppressive effect of xanthan gum was observed at respective concentrations of 0.2 to 0.7%. Moreover, the dl-camphor residual rate increased in Example 4 as compared to Comparative Example 2, and a dl-camphor content decrease-suppressive effect of xanthan gum was observed.

TABLE 2

Terpenoid content decrease-suppressive effect of xanthan gum in polyethylene terephthalate eyedrop container (60° C., 2 day preservation)

| | Xanthan gum content (%) | l-Menthol residual rate (%) | dl-Camphor residual rate (%) |
| --- | --- | --- | --- |
| Example 1 | 0.2 | 80.4 | — |
| Example 2 | 0.5 | 86.8 | — |
| Example 3 | 0.7 | 89.2 | — |
| Example 4 | 0.5 | — | 95.9 |
| Comparative Example 1 | 0 | 74.7 | — |
| Comparative Example 2 | 0 | — | 80.3 |

Experimental Example 2

Terpenoid Content Decrease-Suppressive Effect of Xanthan Gum in Polyethylene Terephthalate Eyedrop Container

TABLE 3

| Components added (g/100 mL) | Ex. 5 | Ex. 6 | Ex. 7 | Comp. Ex. 3 | Comp. Ex. 4 | Comp. Ex. 5 |
|---|---|---|---|---|---|---|
| Xanthan gum | 0.5 | 0.5 | 0.5 | — | — | — |
| Sodium chloride | 0.9 | 0.9 | 0.9 | 0.9 | 0.9 | 0.9 |
| l-Menthol | 0.002 | 0.03 | 0.05 | 0.002 | 0.03 | 0.05 |
| Polysorbate80 | — | — | 0.2 | — | — | 0.2 |
| Purified water | q.s. | q.s. | q.s. | q.s. | q.s. | q.s. |

1. Test Method

The ophthalmic solutions of Examples 5 to 7 and Comparative Examples 3 to 5 were each filled in a 15 mL polyethylene terephthalate eyedrop container and preserved at 60° C. for 2 days. The l-menthol content of each sample before and after the preservation was measured in the same manner as in Experimental Example 1.

2. Test Result

As shown in Table 4, the l-menthol residual rate increased in Examples 5 to 7 as compared to Comparative Examples 3 to 5. An l-menthol content decrease-suppressive effect of xanthan gum was observed at any concentration of l-menthol.

TABLE 4

Menthol content decrease-suppressive effect of xanthan gum (60° C., 2 day preservation)

| | Xanthan gum content (%) | l-Menthol content (%) | l-Menthol residual rate (%) |
|---|---|---|---|
| Example 5 | 0.5 | 0.002 | 90.1 |
| Example 6 | 0.5 | 0.03 | 91.5 |
| Example 7 | 0.5 | 0.05 | 97.7 |
| Comparative Example 3 | 0 | 0.002 | 78.6 |
| Comparative Example 4 | 0 | 0.03 | 71.4 |
| Comparative Example 5 | 0 | 0.05 | 86.2 |

Experimental Example 3

Menthol Content Decrease-Suppressive Effect of Xanthan Gum in Polypropylene Or Polyethylene Eyedrop Container 1. Test Method The ophthalmic solutions of Example 2 and Comparative Example 1 were filled in a 15 mL polypropylene eyedrop container and a 15 mL polyethylene eyedrop container, respectively, and preserved at 60° C. for 6 hr. The l-menthol content of each sample before and after the preservation was measured in the same manner as in Experimental Example 1.

2. Test Results

As shown in Table 5, the l-menthol residual rate in Example 2 increased as compared to Comparative Example 1 in both polypropylene eyedrop container and polyethylene eyedrop container. Hence, an l-menthol content decrease-suppressive effect of xanthan gum was observed.

TABLE 5

Menthol content decrease-suppressive effect of xanthan gum in polypropylene or polyethylene eyedrop container (60° C., 6 hr preservation)

| | Xanthan gum content (%) | l-Menthol residual ratio (%) | |
|---|---|---|---|
| | | Polypropylene | Polyethylene |
| Example 2 | 0.5 | 53.0 | 23.5 |
| Comparative Example 1 | 0 | 47.2 | 15.5 |

Experimental Example 4

Menthol Content Decrease-Suppressive Effect of Xanthan Gum in Polyethylene Terephthalate Container Piece 1. Test Method The ophthalmic solutions of Example 2 and Comparative Example 1 (5 mL each) were filled in 5 mL glass ampoules, a piece of a polyethylene terephthalate container (about 3 g of about 5 mm×25 mm piece cut out from the body of container) was immersed therein, and the ampoules were preserved at 60° C. for 1 day. The l-menthol content of each sample before and after the preservation was measured in the same manner as in Experimental Example 1. In addition, one free of immersion of a container piece was treated in the same manner.

2. Test Results

As shown in Table 6, the l-menthol residual rate increased in Example 2 as compared to Comparative Example 1. From this result, it is considered that xanthan gum suppressed adsorption of menthol to the container as one mechanism of the content decrease-suppressive effect.

TABLE 6

Menthol content decrease-suppressive effect of xanthan gum in polyethylene terephthalate container (60° C., 1 day preservation)

| | | l-Menthol residual rate (%) | |
|---|---|---|---|
| | Xanthan gum content (%) | No container piece | With container piece |
| Example 2 | 0.5 | 100.4 | 96.7 |
| Comparative Example 1 | 0 | 100.1 | 91.1 |

Formulation examples of the ophthalmic solution comprising xanthan gum and terpenoid of the present invention are shown below.

Example 8

Artificial Lacrimal Fluid Containing Xanthan Gum and l-Menthol

An artificial lacrimal fluid of the following formulation was prepared according to a conventional method.

| Potassium l-aspartate | 0.5 g |
| Aminoethylsulfonic acid | 0.5 g |
| Sodium chloride | 0.5 g |
| Potassium chloride | 0.15 g |
| Boric acid | 0.3 g |

-continued

| | |
|---|---|
| Borax | q.s. |
| Xanthan gum | 0.5 g |
| Benzalkonium chloride | 0.005 g |
| l-Menthol | 0.005 g |
| Purified water | q.s. |
| Total amount | 100 ml (pH 7.2) |

Example 9

Contact Lens Ophthalmic Solution Containing Xanthan Gum and l-Menthol

A contact lens ophthalmic solution of the following formulation was prepared according to a conventional method.

| | |
|---|---|
| Sodium chloride | 0.55 g |
| Potassium chloride | 0.15 g |
| Glucose | 0.005 g |
| Boric acid | 0.6 g |
| Borax | q.s. |
| Xanthan gum | 0.3 g |
| Potassium sorbate | 0.1 g |
| l-Menthol | 0.01 g |
| Macrogol 4000 | 0.3 g |
| Sodium edetate | 0.1 g |
| Purified water | q.s. |
| Total amount | 100 ml (pH 6.5) |

Example 10

Contact Lens Ophthalmic Solution Containing Xanthan Gum and l-Menthol

A contact lens ophthalmic solution of the following formulation was prepared according to a conventional method.

| | |
|---|---|
| Potassium l-aspartate | 0.1 g |
| Sodium chloride | 0.3 g |
| Potassium chloride | 0.05 g |
| Glucose | 0.005 g |
| Boric acid | 1 g |
| Borax | q.s. |
| Sodium citrate | 0.5 g |
| Chlorobutanol | 0.1 g |
| Xanthan gum | 0.3 g |
| Sorbic acid | 0.1 g |
| l-Menthol | 0.035 g |
| Macrogol 4000 | 0.3 g |
| Purified water | q.s. |
| Total amount | 100 ml (pH 6.5) |

Example 11

Non-Prescription Ophthalmic Solution Containing Xanthan Gum and l-Menthol

A non-prescription ophthalmic solution of the following formulation was prepared according to a conventional method.

| | |
|---|---|
| Neostigmine methylsulfate | 0.005 g |
| Panthenol | 0.1 g |
| Potassium l-aspartate | 1 g |
| Allantoin | 0.1 g |
| Chlorpheniramine maleate | 0.03 g |
| Sodium chloride | 0.45 g |
| Sodium l-glutamate | 0.2 g |
| Polyoxyethylene hydrogenated castor oil 60 | 0.3 g |
| l-Menthol | 0.008 g |
| Borneol | 0.002 g |
| Hydrochloric acid | q.s. |
| Benzalkonium chloride | 0.005 g |
| Chlorobutanol | 0.2 g |
| Xanthan gum | 0.5 g |
| Purified water | q.s. |
| Total amount | 100 ml (pH 5.5) |

Example 12

Non-Prescription Ophthalmic Solution Containing Xanthan Gum, dl-Camphor and l-Menthol A non-prescription ophthalmic solution of the following formulation was prepared according to a conventional method.

| | |
|---|---|
| Naphazoline hydrochloride | 0.002 g |
| Allantoin | 0.1 g |
| Zinc sulfate | 0.1 g |
| Chlorpheniramine maleate | 0.03 g |
| Aminoethylsulfonic acid | 0.1 g |
| Boric acid | 0.7 g |
| ε-Aminocaproic acid | 0.2 g |
| Sodium chloride | 0.45 g |
| Chlorobutanol | 0.15 g |
| Methyl paraoxybenzoate | 0.02 g |
| l-Menthol | 0.03 g |
| dl-Camphor | 0.003 g |
| Eucalyptus oil | 0.0009 g |
| Geraniol | 0.0009 g |
| Macrogol 4000 | 0.3 g |
| Xanthan gum | 0.2 g |
| Purified water | q.s. |
| Total amount | 100 ml (pH 5.8) |

Example 13

Non-Prescription Ophthalmic Solution Containing Xanthan Gum and l-Menthol

A non-prescription ophthalmic solution of the following formulation was prepared according to a conventional method.

| | |
|---|---|
| Sodium cromoglycate | 1 g |
| Chlorpheniramine maleate | 0.015 g |
| Pranoprofen | 0.05 g |
| Boric acid | 1.8 g |
| Borax | 0.35 g |
| Sodium edetate | 0.01 g |
| l-Menthol | 0.005 g |

-continued

| | |
|---|---|
| Polysorbate 80 | 0.2 g |
| Xanthan gum | 0.3 g |
| Purified water | q.s. |
| Total amount | 100 ml (pH 7) |

INDUSTRIAL APPLICABILITY

According to the present invention, an ophthalmic solution comprising xanthan gum and terpenoid, which shows a suppressed decrease in the terpenoid content, can be provided. The ophthalmic solution of the present invention provides an excellent feel during use due to a viscous feel free of stickiness and a refreshing feel.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on application No. 2005-201871 filed in Japan, the contents of which are incorporated hereinto by reference.

The invention claimed is:

1. An ophthalmic solution comprising xanthan gum and monoterpene, wherein:
   the concentration of the xanthan gum is 0.2-0.7 w/v % and the concentration of the monoterpene is 0.002-0.05 w/v %,
   the weight ratio of monoterpene:xanthan gum in the ophthalmic solution upon preparation is 1:350-1:4, and
   a container used therefore is a plastic container.

2. The ophthalmic solution of claim 1, wherein the monoterpene is menthol and/or camphor.

3. A method for suppressing a decrease in the content of monoterpene, which comprises adding xanthan gum to an ophthalmic solution comprising monoterpene,
   wherein the concentration of the xanthan gum is 0.2-0.7 w/v % and the concentration of the monoterpene is 0.002-0.05 w/v %, and
   wherein a container used therefore is a plastic container.

4. The method of claim 3, wherein the monoterpene is menthol and/or camphor.

* * * * *